United States Patent
Jaggi et al.

(10) Patent No.: US 6,228,850 B1
(45) Date of Patent: *May 8, 2001

(54) ANTIANGIOGENIC ACTIVITY OF BETULINIC ACID AND ITS DERIVATIVES

(75) Inventors: Manu Jaggi, Haryana; Sunder Ramadoss, New Delhi; Praveen Rajendran, Uttar Pradesh; Mohammad Jamshed Ahmad Siddiqui, Ghaziabad, all of (IN)

(73) Assignee: Dabur Research Foundation, Ghaziabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 09/166,809

(22) Filed: Oct. 6, 1998

Related U.S. Application Data (63) Continuation-in-part of application No. 09/040,856, filed on Mar. 18, 1998, now Pat. No. 6,048,847.

(30) Foreign Application Priority Data

Sep. 30, 1997 (IN) .............................................. 2801/DEL/97
Jul. 27, 1998 (IN) ............................................. 2195/DEL/98

(51) Int. Cl.$^7$ .......................... A61K 31/15; A61K 31/21; A61K 31/56

(52) U.S. Cl. .......................... 514/169; 514/177; 514/178; 514/179; 514/180; 514/181; 514/182; 514/569; 514/570; 514/908; 514/510

(58) Field of Search ..................................... 514/169, 177, 514/178, 179, 180, 181, 182, 908, 510, 569, 570

(56) References Cited

U.S. PATENT DOCUMENTS

| | | | | |
|---|---|---|---|---|
| 5,679,828 | * | 10/1997 | Lee et al. .............................. | 560/116 |
| 5,843,974 | * | 12/1998 | Swift .................................... | 514/370 |
| 5,869,535 | * | 2/1999 | Pezzuto et al. ...................... | 514/640 |
| 5,962,527 | * | 10/1999 | Pezzuto et al. ...................... | 514/569 |
| 6,048,847 | * | 4/2000 | Ramadoss et al. .................. | 514/169 |

FOREIGN PATENT DOCUMENTS

| | | |
|---|---|---|
| 9426695 | 11/1994 | (WO) . |
| 9504526 | 2/1995 | (WO) . |
| 9629068 | 9/1996 | (WO) . |

OTHER PUBLICATIONS

Fujioka, et al, Journal of Natural Products, vol. 57, No. 2, Feb. 1, 1994, pp. 243–247.
Hashimoto, et al, Bioorg. Med., Chem., vol. 5, No. 12, pp. 2133–2143.
Konoshima T. et al., Journal of Natural Products, vol. 50, No. 6, Nov. 1, 1987, pp. 1167–1170.
Miles, D. H., et al., Journal of Pharmaceutical Sciences, vol. 63, No. 4, Apr. 1, 1974, pp. 613–615.
J.S. Lee, et al., Chemical Abstracts+Indexes, vol. 125 No. 19, Nov. 4, 1996, pp. 58.
Bishay, D.W. et al., Bulletin of Pharmaceutical Sciences, vol. 10, Part 2, Jan. 1, 1987, pp. 1–20.
Toda, A. et al, Chemical Abstracts, vol. 127, No. 2, Abstract 023542, Jul. 14, 1997.
Pradhan, B. P., et al, Indian J. Chem., Sect. B., vol. 32B, No. 11, pp. 1178–1180, 1989.
Patra, A. et al., Chemical Abstracts, vol. 111, No. 9, Abstract 078441, Aug. 28, 1989.
Protiva, J. et al, Collection of Czechoslovak Chemical Communications, vol. 42, No. 4, 1977, pp. 1220–1228.
Protiva, J. et al, Collection of Czechoslovak Chemical Communications, vol. 41, No. 4, 1976, pp. 1200–1207.
Protiva, J. et al, Collection of Czechoslovak Chemical Communications, vol. 46, No. 11, 1981, pp. 2734–2741.
Akira Inada, et al., Chemical and Pharmaceutical Bulletin, Vo. 41, No. 3, Mar. 1, 1993, pp. 617–619.
Y. Noda, et al., Chemical and Pharmaceutical Bulletin, vol. 45, No. 10, Jan. 1, 1997, pp. 1665–1670.
Kim, D S H L, et al., Bioorganic & Medical Chemistry Letters, vol. 8, No. 13, Jul. 7, 1998, pp. 1707–1712.
Miller, Craig C., et al. "Oxidative Metabolism of Dihomogammalinolenic Acid by Guinea Pig Epidermis; Evidence of Generation of Anti–Inflammatory Products." Prostaglandins, vol. 35, No. 6 (1988) pp 917–938.
Ziboh, Vincent A., et al. "Dose–response effects of dietary γ–linolenic acid–enriched oils on human polymorphonuclear–neutrophil biosynthesis of leukotriene B4 1–3." American Journal of Clinical Nutrition, No. 55 (1992) pp 39–45.
Ormerod, L. David, et al. "Effects of Altering the Eicosanoid Precursor Pool on Neovascularization and Inflammation in the Alkali–burned Rabbit Cornea." American Journal of Pathology, vol. 137, No. 5 (1990) pp 1243–1252.
Pisha, Emily, et al. "Discovery of betulinic acid as a selective inhibitor of human melanoma that functions by induction of apoptosis." Nature Medicine, vol. 1, No. 10 (1995) pp 1046–1051.
Vanderhoek, Jack, et al. "Regulation of Leukocyte and Platelet Lipoxygenases by Hydroxyeicosanoids." Clinical Pharmacology, vol. 31, No. 21 (1982) pp 3463–3467.
Delporte, Carla L., et al. "Biological Activities and Metabolites from Trevoa trinervis Miers." Phytotherapy Research, vol. II (1997) pp 504–507.
Reich, Reuven, et al. "Eicosapentaenoic Acid Reduces the Invasive and Metastatic Activities of Malignant Tumor Cells." Biochemical and Biophysical Research Communications, vol. 160, No. 2 (1989) pp559–564.

(List continued on next page.)

*Primary Examiner*—Frederick Krass
(74) *Attorney, Agent, or Firm*—Ladas and Parry (57) ABSTRACT

Use of betulinic acid and/or its derivatives for inhibiting and/or preventing angiogenesis is described. Compositions containing betulinic acid derivatives with or without betulinic acid can be used for these purposed.

34 Claims, 3 Drawing Sheets

OTHER PUBLICATIONS

Kanayasu, Toshie, et al. "Eicosapentaenoic Acid Inhibits Tube Formation of Vascular Endothelial Cells in Vitro." Lipids, vol. 26, No. 4 (1991) pp 271–276.

Montesano, Roberto, et al. "Tumor–Promoting Phorbol Esters Induce Angiogenesis In Vitro." Cell, vol. 42 (1985) pp 469–477.

Folkman, J. "Antiangiogenic Therapy." Cancer Principles & Practice of Oncology, Fifth Edition, Chapter 64 (1997) pp 3075–3085.

Setty, Yamaja, et al. "Endothelial Cell Proliferation may be Mediated via the Production of Endogenous Lipoxygenase Metabolites." Biochemical and Biophysical Research Communications, vol. 144, No. 1 (1987) pp 345–351.

Hughes, Sian E. "Functional Characterization of the Spontaneously Transformed Human Umbilical Vein Endothelial Cell Line ECV304: Use in an in Vitro Model of Angiogenesis." Experimental Cell Research 225 (1996) pp 171–185.

* cited by examiner

ANTIANGIOGENIC ACTIVITY OF BETULINIC ACID AND ITS DERIVATIVES

This application is a continuation-in-part of U.S. patent application Ser. No. 09/040,856 filed Mar. 18, 1998 now U.S. Pat. No. 6,048,847.

FIELD OF THE INVENTION

This invention relates to use of betulinic acid and/or its derivatives for inhibiting and/or preventing angiogenesis. This invention also relates to novel betulinic acid derivatives and compositions containing betulinic acid derivatives with or without betulinic acid.

BACKGROUND OF THE INVENTION

Betulinic acid is a pentacyclic triterpene. It has several botanical sources, but can also be chemically derived from betulin, a substance found in abundance in the outer bark of white birch trees (Betula alba). Betulinic acid has been found to selectively kill human melanoma cells (Nature Medicine, Vol.1 (10), 1995, WO 96/29068). The cytotoxic potential of betulinic acid was tested using three human melanoma cell lines, Mel-1, -2, and 4. The growth of all of the cell lines was inhibited significantly by treatment with betulinic acid. The effectiveness of betulinic acid against melanoma cancer cells was also tested using athymic mice. It seems to work by inducing apoptosis in cancer cells.

The anti-cancer activity of betulinic acid and some of its derivatives has also been demonstrated using mouse sarcoma 180 cells implanted s.c. in nude mice (JP 87,301,580), inhibition of growth of P388 lymphocytic leukemia cells in vitro (Choi.Y-H et al., Planta Medica Vol.XLVII,511–513, 1988) and inhibiting growth of cancer cells, particularly by inhibiting ornithine decarboxylase (Yasukawa, K et al, Oncology 48:72–76,1991; WO 95/04526).

Recently, we reported the anti-leukemia and anti-lymphoma activity of betulinic acid and its derivatives with $ED_{50}$ values in the range of approximately 0.5 to 4.0 $\mu$g/ml. and also reported anti-prostate, anti-lung and anti-ovarian cancer activity of betulinic acid and betulinic acid derivatives with $ED_{50}$ values in the range of approximately 0.6 to 6.8 $\mu$g/ml, to 1.3 to 7.7 $\mu$g/ml, and 0.4 to 8.1 $\mu$g/ml respectively (see U.S. application Ser. No. 09/040,856 filed on Mar. 18, 1998 now U.S. Pat. No. 6,048,847, the subject matter of which is incorporated by reference).

The lupanes, and specifically betulinic acid, have been reported to be effective anti-inflammatory agents. (Sotomatsu s., et al; Skin and Urology 21:138,1959 and Inoue H. et al; Chem.Pharm.Bull 2:897–901, 1986). The anti-inflammatory activity of betulinic acid is, at least in part, due to its capacity to inhibit enzymes involved in leukotriene biosynthesis, including 5-lipoxygenase. Betulinic acid and its derivatives have been tested for their ability to inhibit 5-lipoxygenase activity by monitoring their ability to inhibit conversion of linoleic acid to 5-HETE. On pre-incubating with the enzyme, betulinic acid inhibits the production of 5-HETE by approximately 40%. (WO 95/04526).

Angiogenesis is the growth of new microvessels, a process that depends mainly on locomotion, proliferation, and tube formation by capillary endothelial cells. During angiogenesis, endothelial cells emerge from their quiescent state and can proliferate as rapidly as bone marrow cells, but unlike the bone marrow, angiogenesis is usually focal and of brief duration. Pathologic angiogenesis, while still a focal process, persists for months or years. The angiogenesis that occurs in diseases of ocular neovascularisation, arthritis, skin diseases, and tumors rarely terminates spontaneously and has until recently, been difficult to suppress therapeutically. Therefore, the fundamental goal of all antiangiogenic therapy is to return foci of proliferating microvessels to their normal resting state, and to prevent their regrowth (Cancer: Principles & Practice of Oncology, Fifili Edition, edited by Vincent T. DeVita, Jr., Samuel Hellman, Steven A. Rosenberg. Lippincott-Raven Publishers, Philadelphia© 1997).

Although the molecular mechanisms responsible for transition of a cell to angiogenic phenotype are not known, the sequence of events leading to the formation of new vessels has been well documented (Hanahan, D., Science 277, 48–50, 1997). The vascular growth entails either endothelial sprouting (Risau, W., Nature 386, 671–674, 1997) or intussusception (Patan, S., et al; Microvasc. Res. 51, 260–272, 1996). In the first pathway, the following sequence of events may occur: (a) dissolution of the basement of the vessel, usually a postcapillary venule, and the interstitial matrix; (b) migration of endothelial cells toward the stimulus; (c) proliferation of endothelial cells trailing behind the leading endothelial cell (s); (d) formation of lumen (canalization) in the endothelial array/sprout; (e) formation of branches and loops by confluencelanastomoses of sprouts to permit blood flow; (f) investment of the vessel with pericytes; and (g) formation of basement membrane around the immature vessel. New vessels can also be formed via the second pathway: insertion of interstitial tissue columns into the lumen of preexisting vessels. The subsequent growth of these columns and their stabilization result in partitioning of the vessel lumen and remodelling of the local vascular network.

The rationale for antiangiogenic therapy is that progressive tumor growth is angiogenesis-dependent (Folkman, J.; N.Engl.J.Med., 285, 1182, 1971). The switch to the angiogeneic phenotype appears to be an independent event that occurs during the multistage progression to neoplasia. The angiogenic switch itself, while relatively sudden and well localized, is nonetheless a complex process. This phenotype is currently understood in terms of a shift in the net balance of stimulators and inhibitors of angiogenesis, during which inhibitors are downregulated.

Endothelial cell survival and growth are driven by tumor derived mitogens and motogens. These findings have led to a model of tumor growth in which the endothelial cell compartment and the tumor cell compartment interact with each other. They not only stimulate each other's growth, but if the endothelial cells are made unresponsive to angiogenic stimuli from the tumor cells, by administration of a specific endothelial inhibitor, both primary tumors and metastatic tumors can be held dormant at a microscopic size (O'Reilly M S, et al; Cell, 19, 315, 1994 and O'Reilly, MS et al; Nature Med, 2, 689, 1996). One could take advantage of this difference between endothelial cells and tumor cells by administering an angiogenesis inhibitor together with conventional cytotoxic chemotherapy up to the point at which the cytotoxic therapy would normally be discontinued because of toxicity or drug resistance. The angiogenesis inhibitor(s) could then be continued for years, to maintain either stable disease or tumor dormancy. Such combinations of antiangiogenic and cytotoxic therapy in tumor-bearing animals have been curative, whereas either agent alone is merely inhibitory.

Eicosapentanoic acid (EPA), a n-3 polyunsaturated fatty acid found in fish and marine animals is a precursor for eicosanoids. EPA taken by man competes with arachidonic acid for inclusion in cycloxygenase and lipoxygenase pathways. Exposure of endothelial cells to EPA in vitro inhibited their capacity to form tubes—an essential aspect of the angiogenic process and substantially decreases their ability to break through an artificial basement membrane (Matrigel) in vitro (Kanayasu T et al, Lipids 1991;26:271–276). Repeated topical application of EPA in eye drops significantly suppressed the resulting neovascularisation and associated inflammation in induced immunogenic keratitis in rabbit corneas (Verbey N L J, et al, Curr Eye Res 1986; 7:549–557).

A similar effect is observed with gamma linolenic acid (GLA). A number of studies demonstrate that GLA slows cancer growth in animals. GLA also slows angiogenesis. (Ormerod L D et al, Am.J. Pathol. 1990; 137:1243–1252 and Verbey N L J, et al, Curr Eye Res 1986; 7:549–557). The mechanism of this effect is not clear, although GLA supplementation increases certain lipoxygenase products which potently inhibit 5-lipoxygenase enzyme as well as 12-lipoxygenase. (Vanderhoek J Y et al, Biochem. Pharmacol. 1982, 31:3463–3467; Miller C C et al, Prostaglandins 1988; 35: 917–938; Miller C C et al, J. Invest. Dermatol. 1991; 96:98–103; Ziboh V A, Am J Clin Nutr, 1992, 52:39–450). It is conceived that GLA impedes angiogenesis by reducing lipoxygenase activity and thereby slowing the mitotic response of endothelial cells.

The mitotic response of endothelial cells may be mediated, at least in part, by products of the lipoxygenase pathway. When endothelial cells are incubated in culture with fetal calf serum, they multiply at rate that can be quantified. Co-incubation with the lipoxygenase inhibitors NDGA or ETYA substantially reduces their multiplication rate. Although ETYA also inhibits cycloxygenase, the specific cycloxygenase inhibitor indomethacin does not influence endothelial mitosis, suggesting that it is lipoxygenase activity which is crucial to endothelial multiplication. (Setty B N Y et al, Biochem. Biophys. Res. Commn., 1987; 144:345–351).

It has also been shown that some arachidonate derived products of 5-lipoxygenase enhances collagenase production by cancer cells in vitro by inhibiting this enzyme (Reich et al Biochem. Biophys. Res. Commn., 1989; 160:559–564). Collagenase and other lytic enzymes are secreted by endothelial cells to enable migration through basement membranes. Collagenase induction seems to be an obligatory step in angiogenesis, as the metalloproteinase inhibitor 1,10 phenanthroline, which inhibits collagenase but not most other proteolytic enzymes, blocks angiogenesis in vitro (Montesano R, Orci L; Cell 1985; 42:469477).

Certain cancer cells are known to adhere to E-Selectin via E-Selectin ligands on their cell surface and this event is one component of the metastasis process. Betulinic acid and its derivatives interfere with Selectin binding. Betulinic acid inhibited P-Selectin binding to 2,3, sLex, a chemical known to bind to P-Selectin, with an $IC_{50}$ of 125 uM. It also inhibited P-Selectin binding to HL-60 cells in a dose-dependent way with an $IC_{50}$ of 0.75 mM. Betulinic acid and derivatives also significantly interfere with the binding to colon cancer cells, LS 174T to E-Selectin (WO 95/04526).

Several anti-inflammatory agents including fish oil rich in EPA, DHA and DHLA, gamma linolenic acid (GLA) and cromolyn significantly suppress inflammation, angiogenesis and tumor invasiveness. Angiogenesis can thus be viewed as having pathways common with the inflammatory process. Without being limited to a particular mechanism of action, it is surmised that betulinic acid and its derivatives impede angiogenesis by inhibiting 5-lipoxygenase and this subsequently retards tumor growth.

Several angiogenesis inhibitors like Angiostatin, Endostatin, inhibitors of Fibroblast Growth Factor and inhibitors of Vascular Endothelial Growth Factor were found to be antiangiogenic by the virtue of their endothelial cell inhibitory activity (Cancer: Principles & Practice of Oncology, Fifth Edition, 3075–3085, edited by Vincent T. DeVita et al. Lippincott-Raven Publishers, Philadelphia © 1997).

The human umbilical vein endothelial cells (HUVECS) have been used extensively to study the biology and pathobiology of the human endothelial cells including their role in angiogenesis (Exp. Cell Res., 225, 171–185, 1996). Due to the functional and structural endothelial cell heterogeneity between and within species, and the time consuming and difficult isolation and culture methods, a model endothelial cell line has been used that provides standardization of observations. The spontaneously transformed and fully characterized human umbilical vein endothelial cell line ECV304 provides a reproducible and biologically relevant experimental model system for in vitro angiogenesis (In Vitro Cell Dev. Biol., 25, 265–274, 1990). ECV304 cells maintain a stable functional phenotype throughout serial cultivations and exhibit consistent response in in vitro angiogenesis assays (Exp. Cell Res., 225, 171–185, 1996). We have used the ECV304 cell line and report for the first time the antiangiogenic activity of betulinic acid and its derivatives.

SUMMARY OF THE INVENTION

The invention provides a method of preventing, inhibiting and/or treating angiogenesis by administering an effective dosage of betulinic acid, derivatives of betulinc acid or a mixture thereof.

This invention also provides for novel betulinic acid derivatives and compositions containing them with physiologically acceptable additives, diluents, carriers and excipients. The compositions may also include betulinic acid.

These compositions may be used for preventing, treating and/or inhibiting angiogenesis.

A further object of the invention is to provide compounds and compositions for treating, inhibiting and/or preventing angiogenesis using a natural product-derived betulinic acid, and/or its derivatives or a synthetic betulinic acid and/or its derivatives.

Another object of the invention is to provide a treatment method using betulinic acid and/or its derivatives to inhibit angiogenesis, wherein betulinic acid, its derivatives or mixtures thereof is administered systemically.

Yet another object of the invention is to overcome the problem of high toxicity associated with standard antiangiogenic chemotherapeutic agents by using a natural product-derived compound, e.g., betulinic acid, its derivatives or mixtures thereof.

Still another object of the invention is to overcome the problem of insufficient availability associated with synthetic antiangiogenic anticancer agents by using readily available betulinic acid and its semisynthetic derivatives.

Another object of the invention is to overcome the problem of high costs of synthetic antiangiogenic agents by utilizing the readily available natural product derived compound e.g. betulinic acid and its derivatives which is expected to be less expensive than other chemotherapeutic drugs.

These and other objects of the present invention will become apparent from the description of the invention disclosed below, which description is intended to limit neither the spirit or scope of the invention but is only offered as illustrations of the preferred embodiments of the invention.

DETAILED DESCRIPTION OF INVENTION

Betulinic acid and its derivatives inhibit endothelial cell proliferation and exhibit high endothelial cell specificity thereby specifically targeting endothelial cells. Betulinic acid and its derivatives also inhibit the formation of tube-like-structures (TLS) of endothelial cells and this was shown when endothelial cells were grown on Matrigel coated surface. The endothelial cell anti-proliferative activity (see Table I, column titled ECV 304) along with anti-TLS activity very strongly predicts the anti-angiogenic activity of betulinic acid and its derivatives.

Figure 1:
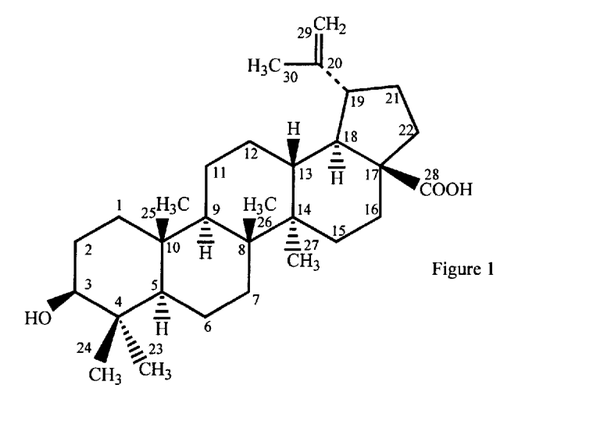
FIG. 1 is a formula representing certain betulinic acid derivatives.

The method of this invention comprises administering a therapeutically effective dose of betulinic acid, betulinic acid derivatives or mixtures thereof either alone or in a pharmaceutical composition so as to kill, inhibit or prevent the multiplication of tumor associated endothelial cells. In a preferred embodiment, pharmaceutically acceptable carriers, diluents, excipients and/or solvents are used with betulinic acid, its derivatives or mixtures thereof. Betulinic acid has the structure Derivatives of betulinic acid according to this invention have a basic skeleton of betulinic acid as shown in FIG. 1 of the accompanying drawings;

wherein R, $R_1$, $R_2$, $R_3$, $R_4$, $R_5$ and $R_6$ independently or in combination represent the following groups:

R is H;

$R_1$ is H, Br, Cl, F or I;

when $R_2$ is H, $R_3$ is OH, $OCOCH_3$, $OCO\ (CH_2)_nCH_3$ (where n=1 to 5),
   $OCOC\ (CH_3)_3$, $OCO\ (CH_2)_nCl$ (where n=1 to 10), $OCOC_6H_5$, $NH_2$,
   $NHCH_2CH_2OH$, $OSO_2CH_3$, $N{=}CHC_6H_4Br$, $N{=}CHC_6H_4Cl$, $N{=}CHC_6H_4NO_2$,
   $NHCH_2CH_2OCOCH_3$, $N{=}CHC_6H_3(CH_3)CF_3$,
   $N{=}CHC_6H_4CF_3$, $N{=}CHC_6H_3Br_2$, $N{=}CHC_6H_3Cl_2$,
   $N{=}CHC_6H_4F$, $OCOC_6H_4Br$, $OCOC_6H_4Cl$, $OCOC_6H_4F$,
   $N{=}CHC_6H_3F_2$, $OCOC_6H_4I$, $OCOC_6H_3Cl_2$, $OCOC_6H_3F_2$,
   $OCOC_6H_2Cl_3$, $OCOCH\ (OCOCH_3)CH_3$, $OCOCH\ (OCOCH_3)C_6H_5$,
   $OCOCH_2C_6H_5$ or $$OCO-\underset{OH}{\overset{H}{\underset{|}{\overset{|}{C}}}}-CH_3,$$

or $R_2$ and $R_3$ together are O, $NNHC_6H_5$, $NNHC_6H_2Cl_3$, $NNHC_6H_4OCH_3$, $NNHC_6H_4Br$, $NNHC_6H_3Cl_2$, $NNHC_6H_3F_2$, $NNHC_6H_4CF_3$, $NNHC_6H_3(CF_3)_2$, $NNHC_6H_4OH$, $NNHC_6H_3\ (Br)(OCH_3)$; $N{-}OX$ (where X is H, $COCH_3$, $CH_2C_6H_5$, or $SO_2C_6H_4CH_3$), $NNHCH_2C_6H_5$, $NNHCH\ (OH)C_6H_5$, or $NNHC_6H_4F$;

when $R_2$ and $R_3$ together is O, this represents a carbonyl group.

$R_4$ is OH, $-OCH_3$, $O(CH_2)_nCOOCH_3$, $O\ (CH_2)_nCOOC_2H_5$, $O(CH_2)_nCOOH$,
   $O\ (CH_2)_nCOCl$ (where n=1 to 5), $OCH_2CH_2OC_2H_5$, $OCH_2CH_2OH$,
   $OCH_2CH_2OCOCH_3$, Cl, $N_3$, $NHNH_2$, $HNNHC_6H_4OMe$, $NHNHC_6H_2Cl_3$,
   $NH_2$ or $NH\ (CH_2)_nCH_3$(where n=0 to 9);

$R_5$ is H or Br;

$R_6$ is $CH_3$, $CH_2Br$, $CH_2OH$, CHO, $CH_2OCOCH_3$, COOH, $COO\ (CH_2)_nOOCH_3$,
   $COO\ (CH_2)_nOOC_2H_5$, $COO\ (CH_2)_nCOOH$ (where n=1 to 5); or $R_5$ and R6 together are $>C{=}CH_2$, or $>CH{-}CH_3$.

The extraction and purification of betulinic acid; as well as processes for preparing derivatives of betulinic acid and formulations of betulinic acid, its derivatives or mixtures thereof is also described in the U.S. application Ser. No. 09/040,856, now U.S. Pat. No. 6,048,847 the subject matter of which is incorporated by reference.

EXAMPLE 1

A suitable formulation of betulinic acid or its derivatives was prepared as follows. Betulinic acid or its derivatives were solubilized in a minimum volume of methanol. Betulinic acid or its derivatives may also be solubilized in isopropyl alcohol, dimethylformamide, dimethylsulfoxide or any other suitable solvent. Substituted beta-cyclodextrin, such as 2-hydroxypropyl beta-cyclodextrin, sulfobutyl ether beta-cyclodextrin was separately dissolved in water to a concentration of approximately 50 to 1000 mg per ml, preferably 250 to 750 mg per ml. The solubilized betulinic acid or its derivative was added in small aliquots to the derivatized beta cyclodextrin solution and sonicated at low temperature until a clear solution developed. The organic solvent was then removed by rotary evaporation and the final solution filtered to give a sterile product. The resulting solution may be lyophilized.

EXAMPLE 2

Preparation of 3-N-Hydroxyethyl Derivative of Betulinic Acid 3-oxo-derivative of betulinic acid or dihydrobetulinic acid dissolved in absolute alcoholic solvent such as methanol or ethanol and to it is added 15–20% alcoholic hydrochloric acid and 2-aminoethanol and the mixture is stirred at room temperature for 30–60 minutes. To this sodium cyanoborohydride is added and the mixture is stirred further at room temperature for approximately 72 hours. The process is worked up by adding water followed by filtration of solid to yield crude product, which was crystallized from alcohol to yield pure 3-N-hydroxyethyl derivative of betulinic acid.

EXAMPLE 3

Preparation of 3-N-Benzylidene Derivative of Betulinic Acid

3-Amino derivative of betulinic acid is dissolved in alcoholic solvent, such as methanol or ethanol and to it is added benzaldehyde or substituted benzaldehyde derivative in the presence or absence of an alkali carbonate, such as sodium or potassium carbonate. The amount of benzaldehyde or substituted benzaldehyde used is an amount slightly in excess to the molar ratio of substrate used. The mixture was stirred for few hours at ambient temperature to approximately 50° C. The reaction mixture was worked up by removing alcohol under vacuum and adding water. The aqueous layer was either filtered or extracted with halogenated organic solvent, followed by evaporation to yield 3-N-benzylidene derivative of betulinic acid.

EXAMPLE 4

Derivatives of betulinic acid were prepared by making substitutions and/or structural changes at C2, C3, and/or C17 positions of betulinic acid by the methods described above or by the methods described in the examples of U.S. application Ser. No. 09/040,856 filed on Mar. 18, 1998, now U.S. Pat. No. 6,048,847 the subject matter of which is incorporated by reference. The derivatives were characterized on the basis of spectral data. Table I to Table V refer to the structures shown in FIGS. 2 to 5 respectively. A total of 21 derivatives are listed in these tables. The $ED_{50}$ values of a number of the derivatives on ECV304 along with endothelial cell specificity for four different tumor cell lines is shown in Tables VII and VIII respectively.

Derivatives of betulinic acid according to FIG. 2 wherein R to F are shown as follows:

R=H; $R_1$=H; $R_2$=H; $R_3$=$OSO_2CH_3$, $OCOCH_3$, $NH_2NHCH_2CH_2OH$, N=$CHC_6H_4Br$, N=$CHC_6H_4Cl$, $OCOC_6H_4Br$ or N=$CHC_6H_4NO_2$; and $R_4$=H.

Figure 2:
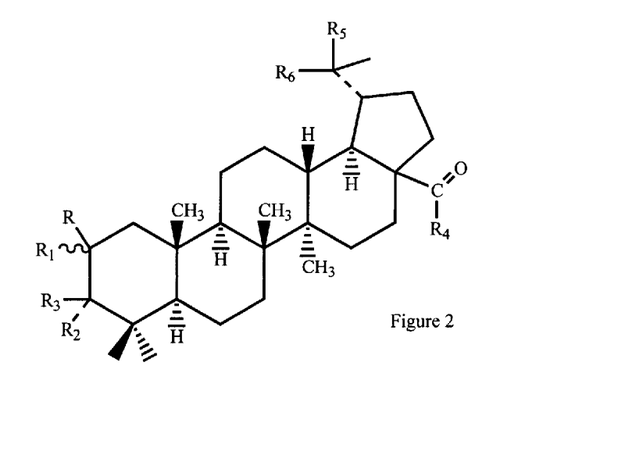
FIG. 2 is a formula representing certain betulinic acid derivatives

Specific derivatives of the formula of FIG. 2 are shown in Table I.

TABLE I

| Derivative | R | $R_1$ | $R_2$ | $R_3$ | $R_4$ |
|---|---|---|---|---|---|
| MJ751-RS | H | H | H | O—$SO_2CH_3$ | H |
| MJ790-RS | H | H | H | $NHCH_2CH_2OH$ | H |

TABLE I-continued

| Derivative | R | $R_1$ | $R_2$ | $R_3$ | $R_4$ |
|---|---|---|---|---|---|
| MJ832-RS | H | H | H | N=CH—$C_6H_4Br(4)$ | H |
| MJ835-RS | H | H | H | N=CH—$C_6H_4Cl(3)$ | H |
| MJ843-RS | H | H | H | O—CO—$C_6H_4Br(2)$ | H |
| MJ780-RS | H | H | H | N=CH—$C_6H_4NO_2(3)$ | H |

NB: Numerals in the parenthesis after the functional groups in the above table indicate the positions of the substituents (e.g. $NO_2$, Cl, or Br) on the benzene ring.

Derivatives of betulinic acid according to FIG. 3 wherein R to $R_4$ are shown as follows:

R=H; $R_1$=H; $R_2$=H; $R_3$=$NH_2$, $OCOCH_3$, OH, $OCOC_6H_5$, $OSO_2CH_3$, N=$CHC_6H_4NO_2$, N=$CHC_6H_4F$, N=$CHC_6H_4NO_2$, N=$CHC_6H_4Br$ or $OCOC_6H_4Br$; and $R_4$=H.

Figure 3:
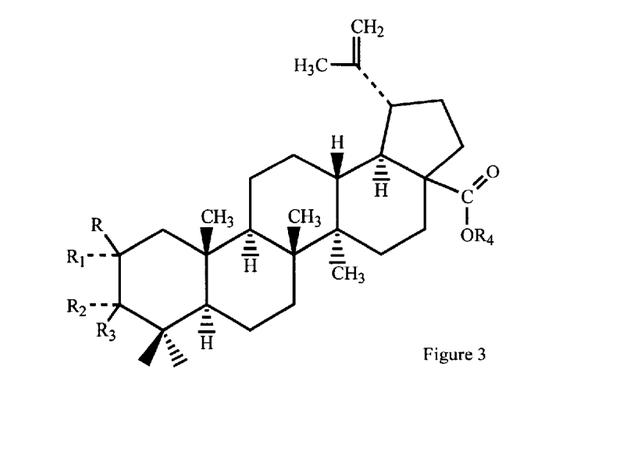
FIG. 3 is a formula representing certain betulinic acid derivatives

Specific derivatives of the formula of FIG. 3 are shown in Table II.

TABLE II

| Derivative | R | $R_1$ | $R_2$ | $R_3$ | $R_4$ |
|---|---|---|---|---|---|
| MJ692-RS | H | H | H | $NH_2$ | H |
| MJ789-RS | H | H | H | O—$SO_2CH_3$ | H |
| MJ839-RS | H | H | H | N=CH—$C_6H_4NO_2(2)$ | H |
| MJ840-RS | H | H | H | N=CH—$C_6H_4F(2)$ | H |
| MJ841-RS | H | H | H | N=CH—$C_6H_4NO_2(3)$ | H |
| MJ842-RS | H | H | H | N=CH—$C_6H_4Br(4)$ | H |
| MJ846-RS | H | H | H | O—CO—$C_6H_4Br(2)$ | H |

NB: Numerals in the parenthesis after the functional groups in the above table indicate the positions of the substituents (e.g. $NO_2$, Br or F) on the benzene ring.

Derivatives of betulinic acid according to FIG. 4 wherein R to $R_3$ are as follows:

R=H; $R_1$=H; $R_2$=O, $NNHC_6H_4OCH_3$, $NNHC_6H_2Cl_3$ or $NNHC_6H_4F$; and $R_3$=H.

Figure 4:
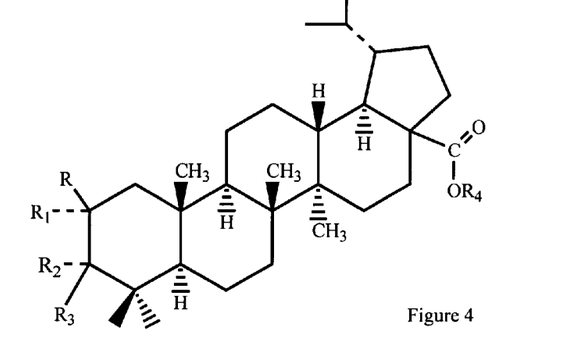
FIG. 4 is a formula representing certain betulinic acid derivatives

Specific derivatives of the formula of FIG. 4 are shown in Table III.

TABLE III

| Derivative | R | $R_1$ | $R_2$ | $R_3$ |
|---|---|---|---|---|
| MJ582-RS | H | H | $NNHC_6H_2Cl_3(2, 4, 6)$ | H |
| MJ826-RS | H | H | $NNHC_6H_4F(4)$ | H |

NB: Numerals in the parenthesis after the functional groups in the above table indicate the positions of the substituents (e.g. Cl, or F) on the benzene ring.

Derivatives of betulinic acid according to FIG. 5 wherein R to $R_3$ are as follows:

R=H, $R_1$=H or Br; $R_2$=NOH, $NNHC_6H_2Cl_3$, $NNHC_6H_4OCH_3$, $NNHCH_2C_6H_5$, $NNHC_6H_4F$, O, $NNHCOC_6H_5$, $NOCH_2C_6H_5$ or NNHCH (OH) $C_6H_5$; and $R_3$=H or $COOCH_2CH_2COOCH_3$.

Figure 5:
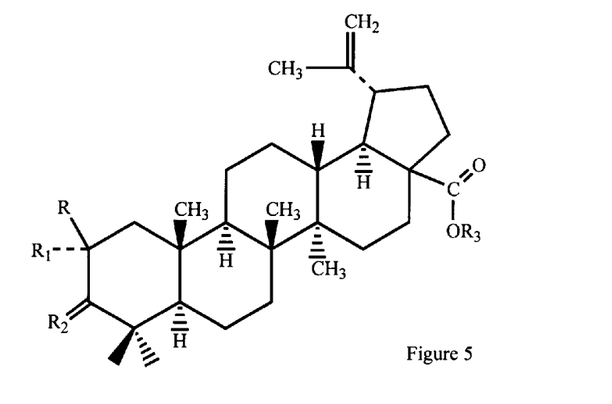
FIG. 5 is a formula representing certain betulinic acid derivatives.

Specific derivatives of the formula of FIG. 5 are shown in Table IV.

TABLE IV

| Derivative | R | $R_1$ | $R_2$ | $R_3$ |
|---|---|---|---|---|
| MJ807-RS | H | H | $NNHCOC_6H_5$ | H |
| MJ813-RS | H | H | N—O—$CH_2C_6H_5$ | H |
| MJ821-RS | H | H | $NNHCH_2C_6H_5$ | H |
| MJ829-RS | H | H | $NNHC_6H_4F$ (4) | H |

TABLE IV-continued

| Derivative | R | $R_1$ | $R_2$ | $R_3$ |
|---|---|---|---|---|
| MJ831-RS | H | H | NNHCH(OH)C$_6$H$_5$ | H |
| MJ874-RS | H | Br | O | COOCH$_2$CH$_2$COOCH$_3$ |

NB: Numerals in the parenthesis after the functional groups in the above table indicate the positions of the substituent (e.g. F) on the benzene ring.

Figure 6:
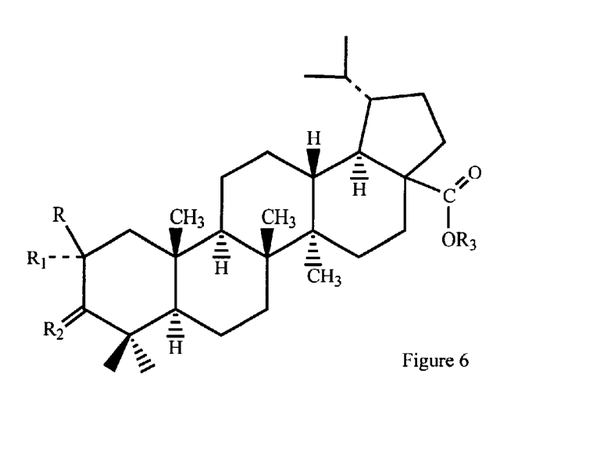
FIG. 6 is a formula representing certain betulinic acid derivatives.

A specific derivative of the formula of FIG. 6 is shown in Table V.

TABLE V

| Derivatives | R | $R_1$ | $R_2$ | $R_3$ | $R_4$ | $R_5$ |
|---|---|---|---|---|---|---|
| MJ542-RS | H | Br | O | H | H | H |

Figure 7:
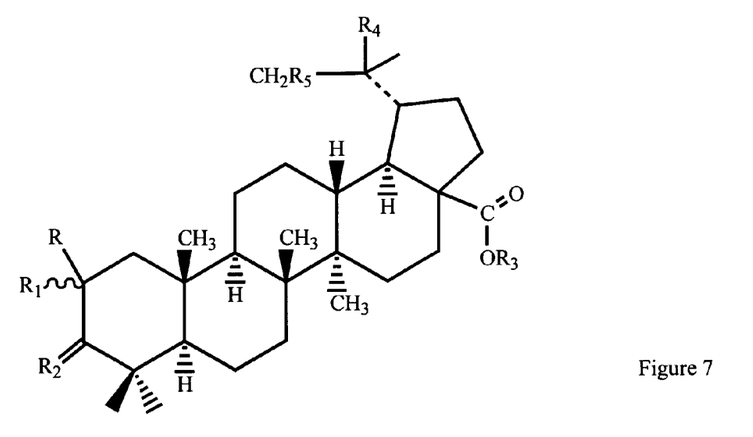
FIG. 7 is a formula representing certain betulinic acid derivatives.
Figure 8:
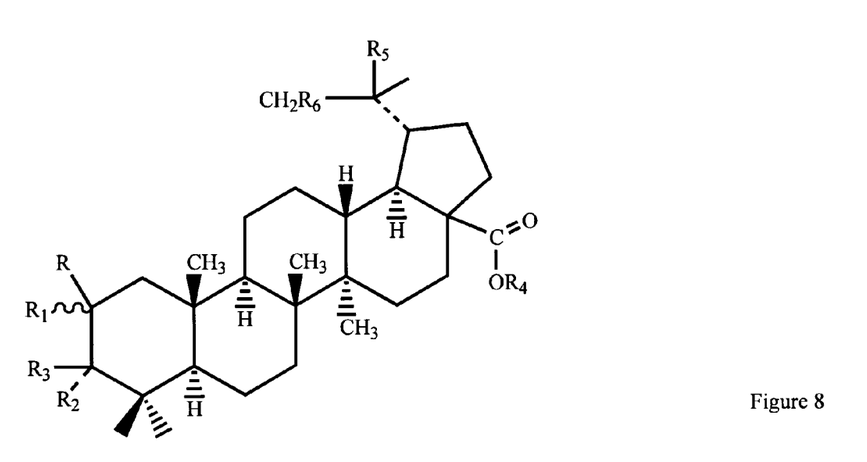
FIG. 8 is a formula representing certain betulinic acid derivatives.

A specific derivative of the formula of FIG. 7 is shown in Table VI.

TABLE VI

| Derivatives | R | $R_1$ | $R_2$ | $R_3$ | $R_4$ | $R_5$ | $R_6$ |
|---|---|---|---|---|---|---|---|
| MJ568-RS | H | Br | H | OH | H | H | H |

EXAMPLE 5

ECV304 cells collected at exponential growth phase were resuspended in medium (3.3×10$^6$ cells/ml in RPMI 1640 containing 10% FBS). 150 µl of medium was added to the wells of a 96-well tissue culture plate (Nunc, Denmark) followed by 30 µl of cell suspension. The plate was left in incubator (37° C., 5% CO$_2$) overnight. 20 µl of betulinic acid or its derivatives was added to marked wells of the 96-well plate so as to obtain a final concentration of 0.5 µg/ml to 10 µg/ml. Each concentration was plated in triplicate. 20 µl of medium alone was added to control wells while wells without cells served as blanks. A total volume of 200 µl was ensured in each well and the plate was left in the incubator (37° C., 5% CO$_2$). After 72 hours of incubation an MTT assay was performed and percentage inhibition in proliferation of treated cells was calculated with respect to control cells.

The cytotoxicty assays for tumor cells have been described in detail in our U.S. application Ser. No. 09/040,856 filed in US on Mar. 18, 1998, now U.S. Pat. No. 6,048,847 which is incorporated by reference. Table VII shows the ED$_{50}$ values of betulinic acid and seventeen derivatives on DU145 (prostate), L132 (lung), A549 (lung) and PA-I (ovary) tumor cells. Table VIII shows the endothelial cell specificity of betulinic acid and seventeen derivatives against DU145 (prostate), L132 (lung), A549 (lung) and PA-I (ovary) tumor cells. The listed derivatives have superior anti-proliferative activity against ECV304 cells with ED$_{50}$ values ranging from 0.21 to 1.25 µg/ml, compared to betulinic acid which has ED$_{50}$ value of 1.26 µg/ml. The endothelial cell specificity was determined by the following formula:

Endothelial cell specificity (ECS) = ED$_{50}$ for tumor cell growth / ED$_{50}$ for endothelial growth.

TABLE VII

| S. No | Derivative | ED$_{50}$ (µg/ml) DU145 | L132 | A549 | PA-1 |
|---|---|---|---|---|---|
| 1 | Betulinic acid | 1.13 ± 0.35 | 1.30 ± 0.55 | >10 | >10 |
| 2 | MJ321-RS | 2.6 ± 0.50 | >10 | >10 | 4.1 ± 0.9 |
| 3 | MJ347-RS | 3.1 ± 1.3 | >10 | >10 | 1.2 ± 0.4 |
| 4 | MJ455-RS | 0.9 ± 0.3 | 2.9 ± 0.7 | 2.3 ± 0.7 | 0.8 ± 0.1 |
| 5 | MJ458-RS | 0.7 ± 0.1 | 2.4 ± 0.1 | 2.2 ± 0.2 | 0.7 ± 0.1 |
| 6 | MJ463-RS | 1.1 ± 0.4 | 1.5 ± 0.6 | 1.8 ± 0.3 | 0.7 ± 0.1 |
| 7 | MJ542-RS | 3.0 ± 0.1 | >10 | >10 | 0.5 ± 0.0 |
| 8 | MJ568-RS | 1.9 ± 0.02 | 0.85 ± 0.12 | 3.1 ± 0.23 | 1.9 ± 0.09 |
| 9 | MJ582-RS | 1.8 ± 0.23 | 1.7 ± 0.2 | 7.7 ± 0.3 | 1.1 ± 0.25 |
| 10 | MJ586-RS | 1.4 ± 0.1 | 2.4 ± 0.4 | 3.9 ± 0.14 | 1.0 ± 0.45 |
| 11 | MJ606-RS | 3.1 ± 0.1 | 2.2 ± 0.24 | 3.9 ± 0.45 | 2.2 ± 0.24 |
| 12 | MJ617-RS | 3.8 ± 0.07 | 0.9 ± 0.23 | 10.3 ± 0.35 | 1.0 ± 0.35 |
| 13 | MJ623-RS | 8.9 ± 0.45 | 10.3 ± 0.2 | 10.3 ± 0.31 | 4.4 ± 0.23 |
| 14 | MJ677-RS | 1.7 ± 0.36 | 4.0 ± 0.2 | 7.3 ± 0.34 | 3.2 ± 0.13 |
| 15 | MJ692-RS | 1.9 ± 0.13 | 10.2 ± 0.34 | 6.6 ± 0.11 | 5.2 ± 0.24 |
| 16 | MJ807-RS | 3.0 ± 0.17 | <0.5 | 10.8 ± 0.46 | 1.6 ± 0.14 |
| 17 | MJ826-RS | 7.6 ± 0.04 | 8.4 ± 0.3 | 9.1 ± 0.11 | 2.7 ± 0.14 |
| 18 | MJ829-RS | 1.2 ± 0.17 | 3.9 ± 0.34 | 7.0 ± 0.03 | 0.49 ± 0.24 |

TABLE VIII

| S.No | Derivative | ECV304 (ED$_{50}$ µg/ml) | Endothelial cell specificity (ECS) for DU145 | L132 | A549 | PA-1 |
|---|---|---|---|---|---|---|
| 1 | Betulinic acid | 1.26 ± 0.44 | 0.9 | 1.1 | >7.9 | >7.93 |
| 2 | MJ321-RS | 1.02 ± 0.25 | 2.5 | >9.8 | >9.8 | 4.01 |
| 3 | MJ437-RS | 0.028 ± 0.005 | 11.1 | >35.7 | >35.7 | 4.28 |
| 4 | MJ455-RS | 1.25 ± 0.77 | 0.7 | 2.3 | 1.8 | 0.64 |
| 5 | MJ458-RS | 0.49 ± 0.29 | 1.4 | 2.9 | 4.5 | 1.42 |
| 6 | MJ463-RS | 0.69 ± 0.21 | 1.6 | 2.2 | 2.6 | 1.01 |
| 7 | MJ542-RS | 0.31 ± 0.14 | 9.7 | >32.3 | >32.3 | 1.61 |
| 8 | MJ568-RS | 0.27 ± 0.02 | 7.0 | 3.1 | 11.5 | 7.0 |
| 9 | MJ582-RS | 0.48 ± 0.23 | 3.7 | 3.5 | 16.1 | 2.3 |
| 10 | MJ586-RS | 0.21 ± 0.03 | 6.6 | 11.4 | 18.6 | 4.8 |
| 11 | MJ606-RS | 0.71 ± 0.12 | 4.3 | 3.1 | 5.5 | 3.1 |
| 12 | MJ617-RS | 0.21 ± 0.007 | 18.1 | 4.3 | 49.0 | 4.8 |
| 13 | MJ623-RS | 0.67 ± 0.45 | 13.3 | 15.4 | 15.4 | 6.6 |
| 14 | MJ677-RS | 0.63 ± 0.16 | 2.7 | 6.3 | 11.6 | 5.0 |
| 15 | MJ692-RS | 0.45 ± 0.35 | 4.2 | 22.6 | 14.7 | 11.6 |
| 16 | MJ807-RS | 0.39 ± 0.07 | 7.7 | <1.2 | 27.7 | 4.1 |
| 17 | MJ826-RS | 0.38 ± 0.14 | 20.0 | 22.1 | 24.0 | 7.1 |
| 18 | MJ829-RS | 0.35 ± 0.07 | 3.4 | 11.1 | 20.0 | 1.4 |

ECS less than 10:Low endothelial cell specificity.
ECS between 10 and 20:Moderate endothelial cell specificity.
ECS greater than 20:High endothelial cell specificity.

We expect that the 'high' and 'moderate' ECS compounds specifically target endothelial cells and can be grouped under potent anti-angiogenic compounds while 'low' ECS compounds would supplement their already reported cytotoxic activity against tumor

EXAMPLE 6

Matrigel (350 ul) was placed into each well of a 24-well culture plate at 4° C. and was allowed to polymerize by incubation at 37° C. for 30 min. ECV304 (1.5×10$^4$) were seeded on the Matrigel in 500 ul DMEM supplemented with 10% FBS. Betulinic acid and five of its derivatives with ED50 values of less than 0.5 µg/ml for ECV304 were added to marked wells at 1 µg/ml and incubated at 37° C. for 12 hours. The absence of cytotoxicity of betulinic acid and its derivatives on ECV304 cells at 12 hours was confirmed by suitable controls. Five different phase-contrast microscopic fields (4X) were viewed and total tube length of the tubelike-structures (TLS) measured using Video Pro 32 Image Analysis system. Percent reduction in total tube length was given as the mean of the data from five fields. Percent inhibition of TLS was calculated with reference to Controls. A qualitative assessment was performed wherein the ability of betulinic acid and its derivatives to inhibit tube formation with reference to Control (Untreated) was rated on a scale of 0 to 4, where "0" indicates "No loss in TLS activity" and "4" indicates "Complete loss of TLS activity" (See Note below the Table-IX).

TABLE IX

| Derivative (1 μg/ml) | % reduction in total tube length | Loss of TLS activity (Qualitative estimation) |
|---|---|---|
| MJ347-RS | 47.6 | 2 |
| MJ568-RS | 28.7 | 2 |
| MJ586-RS | 13.1 | 1 |
| MJ807-RS | 49.2 | 3 |
| MJ829-RS | 18.5 | 3 |
| Betulinic acid | 5.5 | 1 |

Note: 0 No loss in TLS activity
1 Marginal loss of TLS activity
2 Significant loss of TLS activity
3 Near complete loss of TLS activity
4 Complete loss of TLS activity

Systemic administration refers to oral, rectal, nasal, transdermal or parenteral (i.e., intramuscular, intraperitoneal, subcutaneous or intravenous). In accordance with good clinical practice, it is preferred to administer the composition at a dose that will produce antiangiogenic effects without causing undue harmful side effects. The composition may be administered either alone or as a mixture with other therapeutic agents.

The composition of the invention may contain betulinic acid alone, one or more betulinic acid derivatives alone; or betulinic acid and one or more betulinic acid derivatives. Compositions according to this invention contain one or more of a physiologically acceptable additive; carrier, diluent, solvent filler, lubricant, excipient, binder or stabilizer. Compositions may be tablets, lozenges, capsules, powders, aqueous or oily suspensions, syrups, elixirs, implants or aqueous solutions prepared by any conventional method.

Compositions which provide from about 10 mg to 1000 mg of the composition per unit dose are preferred. The nature of pharmaceutical composition employed will, of course, depend on the desired route of administration. The human dosage of the composition is in the range of 1.0 to 200 mg/kg/day and the preferred range is 1.0 to 50 mg/kg/day.

What is claimed is:

1. A method of preventing, treating or inhibiting tumor associated angiogenesis in a patient, said method comprising administering an effective amount of betulinic acid derivative or a combination of betulinic acid and a betulinic acid derivative to a patient in need thereof, wherein the betulinic acid derivative is of the formula wherein R, $R_1$, $R_2$, $R_3$, $R_4$, $R_5$ and $R_6$ independently or in combination represent the following groups:

R is H;

$R_1$ is H, Br, Cl, F or I;

when $R_2$ is H, $R_3$ is OH, $OCOCH_3$, $OCO(CH_2)_nCH_3$ (where n=1 to 5), $OCOC(CH_3)_3$, $OCO(CH_2)_nCl$ (where n=1 to 10), $OCOC_6H_5$, $NH_2$, $NHCH_2CH_2OCOCH_3$, $OSO_2CH_3$, $N=CHC_6H_4Br$, $N=CHC_6H_4Cl$, $N=CHC_6H_4NO_2$, $NHCH_2CH_2OCH_3$, $N=CHC_6H_3(CH_3)CF_3$, $N=CHC_6H_4CF_3$,

$N=CHC_6H_3Br_2$, $N=CHC_6H_3Cl_2$, $N=CHC_6H_4F$, $OCOC_6H_4Br$, $OCOC_6H_4Cl$, $OCOC_6H_4F$, $N=CHC_6H_3F_2$, $OCOC_6H_4I$, $OCOC_6H_3Cl_2$, $OCOC_6H_3F_2$, $OCOC_6H_2Cl_3$, $OCOCH(OCOCH_3)CH_3$, $OCOCH(OCOCH_3)C_6H_5$, $OCOCH_2C_6H_5$ or or $R_2$ and $R_3$ together are O, $NNHC_6H_5$, $HC_6H_2Cl_3$, $NNHC_6H_4OCH_3$, $NNHC_6H_4Br$, $NNHCH_3Cl_2$, $NNHC_6H_3F_2$, $NNHC_6H_4CF_3$, $NNC_6H_3(CF_3)_2$, $NNHC_6H_4OH$, $NNHC_6H_3(Br)(OCH_3)$; N—OX (where X is H, $COCH_3$, $CH_2C_6H_5$, or $SO_2C_6H_4CH_3$), $NNHCH_2C_6H_5$, $NNHCH(OH)C_6H_5$, or $NNHC_6H_4F$;

when $R_2$ and $R_3$ together is O, this represents a carbonyl group;

$R_4$ is $O(CH_2)_nCOOCH_3$, $O(CH_2)_nCOOC_2H_5$, $O(CH_2)_nCOOH$, $O(CH_2)_nCOCl$ (where n=1 to 5), $OCH_2CH_2OC_2H_5$, $OCH_2CH_2OH$, $OCH_2CH_2OCOCH_3$, Cl, $N_3$, $NHNH_2$, $HNNHC_6H_4OMe$, or $NHNHC_6H_2Cl_3$;

R is H or Br;

R is $CH_3$, $CH_2Br$, $CH_2OH$, CHO, $CH_2OCOCH_3$, COOH, $COO(CH_2)_nCOOCH_3$, $COO(CH_2)_nCOOC_2H_5$, $COO(CH_2)_nCOOH$ (where n=1 to 5); or $R_5$ and $R_6$ together are X=$CH_2$, or >CH—$CH_3$.

2. A method as claimed in claim 1, wherein the patient is human, mammal or other animal.

3. A method as claimed in claim 1, wherein the betulinic acid, betulinic acid derivative or mixture thereof is administered to the patient in a pharmaceutically acceptable additive, carrier, diluent, solvent, filler, lubricant, excipient, binder or stabilizer.

4. A method as claimed in claim 1, wherein the betulinic acid, betulinic acid derivative or mixture thereof is administered in the form of a tablet, lozenge, capsule, powder, aqueous or oily suspension, syrup, elixir, implant or aqueous solution.

5. A method as claimed in claim 1, wherein the dosage for human patient is in the range of 1.0 to 200 mg/kg/day.

6. A method as claimed in claim 1, wherein the betulinic acid, the betulinic acid derivative or mixture thereof is administered to the patient systemically.

7. A method as claimed in claim 1, wherein the betulinic acid derivative is of the formula, wherein R=H; $R_1$=H; $R_2$=H; $R_3$=$OSO_2CH_3$, $NHCH_2CH_2OH$, N=$CHC_6H_4Br$, N=$CHC_6H_4Cl$, or N=$CHC_6H_4NO_2$; and $R_4$=H.

8. A method of preventing, treating or inhibiting tumor associated angiogenesis in a patient, said method comprising administering an effective amount of betulinic acid derivative or a combination of betulinic acid and a betulinic acid derivative to a patient in need thereof, wherein the betulinic acid derivative is of the formula wherein

R=H; $R_1$=H; $R_2$=H; $R_3$=$OSO_2CH_3$, N=$CHC_6H_4NO_2$, N=$CHC_6H_4F$, or N=$CHC_6H_4Br$; and $R_4$=H.

9. A method is claimed in claim 1 wherein the betulinic acid derivative is of the formula wherein R=H; $R_1$=H; $R_2$=$NNHC_6H_4OCH_3$, $NNHC_6H_2Cl_3$ or $NNHC_6H_4F$; and $R_3$=H.

10. A method of preventing, treating or inhibiting tumor associated angiogenesis in a patient, said method comprising administering an effective amount of betulinic acid derivative or a combination of betulinic acid and a betulinic acid derivative to a patient in need thereof wherein the betulinic acid derivative is of the formula wherein R=H, $R_1$=H or Br, $R_2$=$NNHC_6H_2Cl_3$, $NNHC_6H_4OCH_3$, $NNHCH_2C_6H_5$, $NNHC_6H_4F$, $NNHCOC_6H_5$, $NOCH_2C_6H_5$ or $NNHCH(OH)C_6H_5$; and $R_3$=H or $COOCH_2CH_2COOCH_3$.

11. A method of preventing, treating or inhibiting tumor associated angiogenesis in a patient, said method comprising administering an effective amount of betulinic acid derivative or a combination of betulinic acid and a betulinic acid derivative to a patient in need thereof, wherein the betulinic acid derivative is of the formula wherein R, $R_3$, $R_4$ and $R_5$ are hydrogen, $R_1$ is Br and $R_2$ is 0.

12. A method of preventing, treating or inhibiting tumor associated angiogenesis in a patient, said method comprising administering an effective amount of betulinic acid derivative or a combination of betulinic acid and a betulinic acid derivative to a patient in need thereof, wherein the betulinic acid derivative is of the formula wherein R, $R_2$, $R_4$, $R_5$ and $R_6$ are H, $R_1$ is Br and $R_3$ is OH.

13. A method for treating leukemia, lymphoma, prostate, lung or ovarian tumors comprising administering an effective amount of a betulinic acid derivative or a combination of a betulinic acid derivative and betulinic acid and another chemotherapy drug to a patient in need of such treatment, wherein the betulinic acid derivative is of the formula wherein R, $R_1$, $R_2$, $R_3$, R4, R5 and R independently or in combination represent the following groups:

R is H;

$R_1$ is H, Br, Cl, F or I;

when $R_2$ is H, $R_3$ is OH, $OCOCH_3$, $OCO(CH_2)_nCH_3$ (where n=1 to 5), $OCOC(CH_3)_3$, $OCO(CH_2)_nCl$ (where n=1 to 10), $OCOC_6H_5$, $NH_2$, $NHCH_2CH_2OCOCH_3$, $OSO_2CH_3$, $N=CHC_6H_4Br$, $N=CHC_6H_4C_1$, $N=CHC_6H_4NO_2$, $NHCH_2CH_2OCH_3$, $N=CHC_6H_3(CH_3)CF_3$, $N=CHC_6H_4CF_3$,

$N=CHC_6H_3Br_2$, $N=CHC_6H_3Cl_2$, $N=CHC_6H_4F$, $OCOC_6H_4Br$, $OCOC_6H_4Cl$, $OCOC_6H_4F$, $N=CHC_6H_3F_2$, $OCOC_6H_4I$, $OCOC_6H_3Cl_2$, $OCOC_6H_3F_2$, $OCOC_6H_2Cl_3$, $OCOCH(OCOCH_3)CH_3$, $OCOCH(OCOCH_3)C_6H_5$, $OCOCH_2C_6H_5$ or or $R_2$ and $R_3$ together are O, $NNHC_6H_5$, $NNHC_6H_2Cl_3$, $NNHC_6H_4OCH_3$, $NNHC_6H_4Br$, $NNHC_6H_3Cl_2$, $NNHC_6H_3F_2$, $NNHC_6H_4CF_3$, $NNC_6H_3(CF_3)_2$, $NNHC_6H_5$, $NNHC_6H_3(Br)(OCH_3)$; N—OX (where X is H, $COCH_3$, $CH_2C_6H_5$, or $SO_2C_6H_4CH_3$), $NNHCH_2C_6H_5$, $NNHCH(OH)C_6H_5$, or $NNHC_6H_4F$;

when $R_2$ and $R_3$ together is O, this represents a carbonyl group;

$R_4$ is $O(CH_2)_nCOOCH_3$, $O(CH_2)_nCOOC_2H_5$, $O(CH_2)_nCOOH$, $O(CH_2)_nCOCl$ (where n=1 to 5), $OCH_2CH_2OC_2H_5$, $OCH_2CH_2OH$,

$OCH_2CH_2OCOCH_3$, Cl, $N_3$, $NHNH_2$, $HNNHC_6H_4OMe$, $NHNHC_6H_2Cl_3$, or;

$R_5$ is H or Br;

$R_6$ is $CH_3$, $CH_2Br$, $CH_2OH$, CHO, $CH_2OCOCH_3$, COOH, $COO(CH_2)_nCOOCH_3$, $COO(CH_2)_nCOOC_2H_5$, $COO(CH_2)_nCOOH$ (where n=1 to 5); or $R_5$ and R, together are >$CH_2$, or >CH—$CH_3$.

14. A method of preventing, treating or inhibiting tumor associated angiogenesis in a patient, said method comprising administering an effective amount of betulinic acid derivative or a combination of betulinic acid and a betulinic acid derivative to a patient in need thereof, wherein the betulinic acid derivative is of the formula wherein R, $R_1$, $R_2$, $R_3$, $R_4$, $R_5$ and $R_6$ independently or in combination represent the following groups:

R is H;

$R_1$ is H, Br, Cl, F or I;

$R_2$ and $R_3$ together are $NNHC_6H_5$, $NNHC_6H_2Cl_3$, $NNHC_6H_4OCH_3$, $NNHC_6H_4Br$, $NNHC_6H_3Cl_2$, $NNHC_6H_3CF_2$, $NNHC_6H_4CF_3$, $NNHC_6H_3(CF_3)_2$, $NNHC_6H_4OH$, $NNHC_6H_3(BR)(OCH_3)$; N—OX (where X is $CH_2C_6H_5$, or $SO_2C_6H_5CH_3$), $NNHCH_2C_6H_5$, $NNHCH(OH)C_6H_5$, or $NNHC_6H_4F$;

R$_4$ is OH, OCH$_3$, O(CH$_2$)$_n$COOCH$_3$, O(CH$_2$)$_n$COOC$_2$H$_5$, O(CH$_2$)$_n$COOH, O(CH$_2$)$_N$COCl(where n=1 to 5), OCH$_2$CH$_2$CH$_2$OC$_2$H$_5$, OCH$_2$CH$_2$OH, OCH$_2$CH)$_2$ OCOCH$_3$, Cl, N$_3$, NHNH$_2$, HNNHC$_6$H$_4$Ome, NHNHC$_6$H$_2$Cl$_3$, NH$_2$or NH(CH$_2$)$_n$CH$_3$ (where n=0 to 9);

R$_5$ is H or Br;

R$_6$ is CH$_3$; CH$_2$Br, C$_2$OH, CHO, CH$_2$OCOCH$_3$, COOH, COO(CH$_2$)$_n$COOCH$_3$, COO(CH$_2$)$_n$COOC$_2$H$_5$, COO(CH$_2$)$_n$COOH (where n=1 to 5); or R$_5$ and R$_6$ together are >C=CH$_2$, or >CH—CH$_3$.

15. A method for treating leukemia, lymphoma, prostate, lung or ovarian tumors comprising administering an effective amount of betulinic acid derivative or a combination of betulinic acid and a betulinic acid derivative to a patient in need thereof wherein the betulinic acid derivative is of the formula wherein R, R$_1$, R$_2$, R$_3$, R$_4$, R$_5$ and R$_6$ independently or in combination represent the following groups:

R is H;

R$_1$ is H, Br, Cl, F or I;

R$_2$ and R$_3$ together are NNHC$_6$H$_5$, NNHC$_6$H$_2$Cl$_3$, NNHC$_6$H$_4$OCH$_3$, NNHC$_6$H$_4$Br, NNHC$_6$H$_3$C$_{12}$, NNHC$_6$H$_3$F$_2$, NNHC$_6$H$_4$CF$_3$, NNC$_6$H$_3$(CF$_3$)$_2$, NNHC$_6$H$_4$OH, NNHC$_6$H$_3$(Br)(OCH$_3$); N—OX (where X is CH$_2$C$_6$H$_5$, or SO$_2$C$_6$H$_4$CH$_3$), NNHCH$_2$C$_6$H$_5$, NNHCH(OH)C$_6$H$_5$, or NNHC$_6$H$_4$F;

R$_4$ is OH, OCH$_3$, O(CH$_2$)$_n$COOCH$_3$, O(CH$_2$)$_n$COOC$_2$H$_5$, O(CH$_2$)$_n$COOH, O(CH$_2$)$_n$COCl (where n=1 to 5), OCH$_2$CH$_2$OC$_2$H$_5$, OCH$_2$CH$_2$OH, OCH$_2$CH$_2$OCOCH$_3$, Cl, N$_3$, NHNH$_2$, HNNHC$_6$H$_4$OMe, NHNHC$_6$H$_2$Cl$_3$, NH$_2$ or NH(CH$_2$)$_n$CH$_3$ (where n=0 to 9);

R$_5$ is H or Br;

R$_6$ is CH$_3$, CH$_2$Br, CH$_2$OH, CHO, CH$_2$OCOCH$_3$, COOH, COO(CH$_2$)$_n$COOCH$_3$, COO(CH$_2$)$_n$COOC$_2$H$_5$, COO(CH$_2$)$_n$COOH (where n=1 to 5); or R$_5$ and R$_6$ together are >C=CH$_2$, or >CH—CH$_3$.

16. A method of preventing, treating or inhibiting tumor associated angiogenesis in a patient, said method comprising administering an effective amount of betulinic acid derivative or a combination of betulinic acid and a betulinic acid derivative to a patient in need thereof, wherein the betulinic acid derivative is of the formula wherein R, R$_1$, R$_2$, R$_3$, R$_4$, R$_5$ and R$_6$ independently or in combination represent the following groups:

R is H;

R$_1$ is H, Br, Cl, F or I;

R$_2$ is H, R$_3$ is OCO(CH$_2$)$_n$Cl (where n=1 to 10), NHCH$_2$CH$_2$OCOCH$_3$, OSO$_2$CH$_3$, N=CHC$_6$H$_4$Br, N=CHC$_6$H$_4$Cl, N=CHC$_6$H$_4$NO$_2$, NHCH$_2$CH$_2$OCH$_3$, N=CHC$_6$H$_3$(CH$_3$)CF$_3$, N=CHC$_6$H$_4$CF$_3$, N=CHC$_6$H$_3$Br$_2$, N=CHC$_6$H$_3$Cl$_2$, N=CHC$_6$H$_4$F, N=CHC$_6$H$_3$ F$_2$, OCOC$_6$H$_3$Cl$_2$, OCOC$_6$H$_3$F$_2$, OCOC$_6$H$_2$Cl$_3$, OCOCH(OCOCH$_3$)CH$_3$, OCOCH(OCOCH$_3$)C$_6$H$_5$, OCOCH$_2$C$_6$H$_5$ or

R$_4$ is O(CH$_2$)$_n$COOCH$_3$, O(CH$_2$)$_n$COOC$_2$H, O(CH$_2$)$_n$COOH, O(CH$_2$)$_n$COCl (where n=1 to 5), OCH$_2$CH$_2$OC$_2$H$_5$, OCH$_2$CH$_2$OH, OCH$_2$CH$_2$OCOCH$_3$, Cl, N$_3$, NHNH$_2$, HNNHC$_6$H$_4$ OMe, NHNHC$_6$H$_2$Cl$_3$, NH$_2$ or NH(CH$_2$)$_n$ CH$_3$ (where n =0 to 9);

R$_5$ is H or Br;

R is CH$_3$, CH$_2$Br, CH$_2$OH, CHO, CH$_2$OCOCH$_3$, COOH, COO(CH$_2$)$_n$COOCH$_3$, COO(CH$_2$)$_n$COOC$_2$H$_5$, COO(CH$_2$)$_n$COOH (where n=1 to 5); or R$_5$ and R together are >C=CH$_2$, or >CH—CH$_3$.

17. A method for treating leukemia, lymphoma, prostate, lung or ovarian tumors comprising administering an effective amount of a betulinic acid derivative or a combination of a betulinic acid derivative and betulinic acid and another chemotherapy drug to a patient in need of such treatment, wherein the betulinic acid derivative is of the formula wherein R, R$_1$, R$_2$, R$_3$, R$_4$, R$_5$ and R$_6$ independently or in combination represent the following groups:

R is H;

R, is H, Br, Cl, F or I;

$R_2$ is H, $R_3$ is $OCO(CH_2)_nCl$ (where n=1 to 10),
$NHCH_2CH_2OCOCH_3$, $OSO_2CH_3$, $NCHC_6H_4Br$,
$N=CHC_6H_4Cl$, $N=CHC_6H_4NO_2$,
$NHCH_2CH_2OCH_3$, $N=CHC_6H_3(CH_3)CF_3$,
$N=CHC_6H_4CF_3$,
$N=CHC_6H_3Br_2$, $N=CHC_6H_3Cl_2$,
$N=CHC_6H_4F$, $N=CHC_6H_3F_2$, $OCOC_6H_3Cl_2$,
$OCOC_6H_3F_2$,
$OCOC_6H_2Cl_3$, $OCOCH(OCOCH_3)CH_3$, OCOCH
$(OCOCH_3)C_6H_5$,
$OCOCH_2C_6H_5$ or

$R_4$ is $O(CH_2)_nCOOCH_3$, $O(CH_2)_nCOOC_2H_5$, $O(CH_2)_n$
COOH, $O(CH_2)_nCOCl$ (where n=1 to 5),
$OCH_2CH_2OC_2H_5$, $OCH_2CH_2OH$,
$OCH_2CH_2OCOCH_3$, Cl, $N_3$, $NHNH_2$,
$HNNHC_6H_4OMe$, $NHNHC_6H_2Cl_3$, $NH_2$ or $NH(CH_2)_n$
$CH_3$ (where n=0 to 9);

$R_5$ is H or Br;

$R_6$ is $CH_3$, $CH_2Br$, $CH_2OH$, CHO, $CH_2OCOCH_3$, COOH,
$COO(CH_2)_nCOOCH_3$, $COO(CH_2)_nCOOC_2H_5$, COO
$(CH_2)_nCOOH$ (where n=1 to 5); or $R_5$ and $R_6$ together are $>C=CH_2$, or $>CH—CH_3$.

18. A method of preventing, treating or inhibiting tumor associated angiogenesis in a patient, said method comprising administering an effective amount of betulinic acid derivative or a combination of betulinic acid and a betulinic acid derivative to a patient in need thereof, wherein the betulinic acid derivative is of the formula wherein R, $R_1$, $R_2$, $R_3$, $R_4$, $R_5$ and $R_6$ independently or in combination represent the following groups:

R is H;

$R_1$ is H, Br, Cl, F or I;

$R_2$ is H, $R_3$ is $OCO(CH_2)_nCl$ (where n =1 to 10),
$OCOC_6H_5$, $NH_2$, $NHCH_2CH_2OCOCH_3$, $OSO_2CH_3$,
$N=CHC_6H_4Br$, $N=CHC_6H_4Cl$,
$N=CHC_6H_4NO_2$, $NHCH_2CH_2OCH_3$, $N=CHC_6H_3$
$(CH_3)CF_3$,
$N=CHC_6H_4CF_3$, $N=CHC_6H_3Br_2$, $N=CHC_6H_3Cl_2$,
$N=CHC_6H_4F$, $OCOC_6H_4Br$, $OCOC_6H_4Cl$,
$OCOC_6H_4F$, $N=CHC_6H_3F_2$, $OCOC_6H_4I$, $OCOC_6H_3Cl_2$,
$OCOC_6H_3F_2$, $OCOC_6H_2Cl_3$, $OCOCH(OCOCH_3)CH_3$,
$OCOCH(OCOCH_3)C_6H_5$, $OCOCH_2C_6H$, or

$R_4$ is $O(CH_2)_nCOOCH_3$, $O(CH_2)COOC_2H_5$, $O(CH_2)_n$
COOH, $O(CH_2)_nCOCl$ (where n=1 to 5),
$OCH_2CH_2C_2H_5$, $OCH_2CH_2OH$, $OCH_2CH_2OCOCH_3$,
Cl, $N_3$, $NHNH_2HNNHC_6H_4OMe$, $NHNHC_6H_2Cl_3$,
$NH_2$ or $NH(CH_2)_nCH_3$ (where n=0 to 9);

$R_5$ is H or Br;

$R_6$ is $CH_3$, $CH_2Br$, $CH_2OH$, CHO, $CH_2OCOCH_3$, COOH,
$COO(CHD,COOCH_3$, $COO(CH_2)_nCOOC_2H_5$, COO
$(CH_2)_nCOOH$ (where n=1 to 5); or $R_5$ and $R_6$ together are $>C=CH_2$, or $>CH—CH_3$.

19. A method for treating leukemia, lymphoma, prostate, lung or ovarian tumors comprising administering an effective amount of a betulinic acid derivative or a combination of a betulinic acid derivative and betulinic acid and another chemotherapy drug to a patient in need of such treatment, wherein the betulinic acid derivative is of the formula wherein R, $R_1$, $R_2$, $R_3$, $R_4$, $R_5$ and $R_6$ independently or in combination represent the following groups:

R is H;

$R_1$ is H, Br, Cl, F or I;

$R_2$ is H, $R_3$ is $OCO(CH_2)_nCl$ (where n=1 to 10),
$OCOC_6H_5$, $NH_2$ $NHCH_2CH_2OCOCH_3$, $OSO_2CH_3$,
$N=CHC_6H_4Br$, $N=CHC_6H_4Cl$,
$N=CHC_6H_4NO_2$, $NHCH_2CH_2OCH_3$, $N=CHC_6H_3$
$(CH_3)CF_3$,
$N=CHC_6H_4CF_3$, $N=CHC_6H_3Br_2$, $N=CHC_6H_3Cl_2$,
$N=CHC_6H_4F$, $OCOC_6H_4Br$, $OCOC_6H_4Cl$,
$OCOC_6H_4F$, $N=CHC_6H_3F_2$, $OCOC_6H_4I$, $OCOC_6H_3Cl_2$,
$OCOC_6H_3F_2$, $OCOC_6H_2Cl_3$, $OCOCH(OCOCH_3)CH_3$,
$OCOCH(OCOCH_3)C_6H_5$, $OCOCH_2C_6H$, or $R_4$ is $O(CH_2)_nCOOCH_3$, $O(CH_2)_nCOOC_2H_5$, $O(CH_2)_n$
COOH, $O(CH_2)_nCOCl$ (where n=1 to 5), $OCH_2CH_2OC_2H_5$,
$OCH_2CH_2OH$, $OCH_2CH_2OCOCH_3$, Cl, $N_3$, $NHNH_2$,

HNNHC$_6$H$_4$OMe, NHNHC$_6$H$_2$Cl$_3$, NH$_2$ or NH(CH$_2$)$_n$CH$_3$ (where n =0 to 9);

R$_5$ is H or Br;

R$_6$ is CH$_3$, CH$_2$Br, CH$_2$OH, CHO, CH$_2$OCOCH$_3$, COOH, COO(CH$_2$)$_n$COO)$_3$, COO(CH$_2$)$_n$COOC$_2$H$_5$, COO(CH$_2$)$_n$COOH (where n=1 to 5); or R$_5$ and R$_6$ together are >C=CH$_2$, or >CH—CH$_3$.

20. A method as claimed in claim 1 wherein the betulinic acid derivative is of the formula wherein R=H, R$_1$=Br, R$_2$=NOH, O,NNHC$_6$H$_2$Cl$_3$, NNHC$_6$H$_4$OCH$_3$, NNHCH$_2$C$_6$H$_5$, NNHC$_6$H$_4$F, NNHCOC$_6$H$_5$, NOCH$_2$C$_6$H$_5$ or NNHCH(OH)C$_6$H$_5$; and R$_3$=H or COOCH$_2$CH$_2$COOCH$_3$.

21. A method as claimed in claim 13 wherein the betulinic acid derivative or mixture of betulinic acid derivative and betulinic acid is administered to the patient in a pharmaceutically acceptable additive, carrier, diluent, solvent, filler, lubricant, excipient, binder or stabilizer.

22. A method as claimed in claim 14, wherein the betulinic acid derivative or mixture of betulinic acid derivative and betulinic acid is administered to the patient in a pharmaceutically acceptable additive, carrier, diluent, solvent, filler, lubricant, excipient, binder or stabilizer.

23. A method as claimed in claim 15, wherein the betulinic acid derivative or mixture of betulinic acid derivative and betulinic acid is administered to the patient in a pharmaceutically acceptable additive, carrier, diluent, solvent, filler, lubricant, excipient, binder or stabilizer.

24. A method as claimed in claim 16, wherein the betulinic acid derivative or mixture of betulinic acid derivative and betulinic acid is administered to the patient in a pharmaceutically acceptable additive, carrier, diluent, solvent, filler, lubricant, excipient, binder or stabilizer.

25. A method as claimed in claim 17, wherein the betulinic acid derivative or mixture of betulinic acid derivative and betulinic acid is administered to the patient in a pharmaceutically acceptable additive, carrier, diluent, solvent, filler, lubricant, excipient, binder or stabilizer.

26. A method as claimed in claim 18, wherein the betulinic acid derivative or mixture of betulinic acid derivative and betulinic acid is administered to the patient in a pharmaceutically acceptable additive, carrier, diluent, solvent, filler, lubricant, excipient, binder or stabilizer.

27. A method as claimed in claim 19, wherein the betulinic acid derivative or mixture of betulinic acid derivative and betulinic acid is administered to the patient in a pharmaceutically acceptable additive, carrier, diluent, solvent, filler, lubricant, excipient, binder or stabilizer.

28. A method as claimed in calim 16, wherein the betulinic acid derivative or mixture of betulinic acid derivative and betulinic acid administered in the form of a tablet, lozenge, capsule, powder, aqueous or oily suspension, syrup, elixir, implant or aqueous solution.

29. A method as claimed in claim 14, wherein the betulinic acid derivative or mixture of betulinic acid derivative and betulinic acid administered in the form of a tablet, lozenge, capsule, powder, aqueous or oily suspension, syrup, elixir, implant or aqueous solution.

30. A method as claimed in claim 15, wherein the betulinic acid derivative or mixture of betulinic acid derivative and betulinic acid administered in the form of a tablet, lozenge, capsule, powder, aqueous or oily suspension, syrup, elixir, implant or aqueous solution.

31. A method as claimed in claim 16, wherein the betulinic acid derivative or mixture of betulinic acid derivative and betulinic acid administered in the form of a tablet, lozenge, capsule, powder, aqueous or oily suspension, syrup, elixir, implant or aqueous solution.

32. A method as claimed in claim 17, wherein the betulinic acid derivative or mixture of betulinic acid derivative and betulinic acid administered in the form of a tablet, lozenge, capsule, powder, aqueous or oily suspension, syrup, elixir, implant or aqueous solution.

33. A method as claimed in claim 18, wherein the betulinic acid derivative or mixture of betulinic acid derivative and betulinic acid administered in the form of a tablet, lozenge, capsule, powder, aqueous or oily suspension, syrup, elixir, implant or aqueous solution.

34. A method as claimed in claim 19, wherein the betulinic acid derivative or mixture of betulinic acid derivative and betulinic acid administered in the form of a tablet, lozenge, capsule, powder, aqueous or oily suspension, syrup, elixir, implant or aqueous solution.

* * * * *